United States Patent [19]

Eck et al.

[11] Patent Number: 5,659,032

[45] Date of Patent: Aug. 19, 1997

[54] PROCESS FOR THE SYNTHESIS OF 2,4,6,8-TETRANITRO-2,4,6,8-TETRAAZABICYCLO (3.3.0) OCTANE

[75] Inventors: Geneviève Eck, Ris Orangis; Marc Piteau, Itteville, both of France

[73] Assignee: Societe Nationale Des Poudres et Explosifs, Paris, France

[21] Appl. No.: 392,335

[22] Filed: Feb. 21, 1995

[30]  Foreign Application Priority Data

Feb. 22, 1994 [FR] France .................. 94 01969

[51] Int. Cl.$^6$ ........................... C07D 471/00
[52] U.S. Cl. ........................... 544/350
[58] Field of Search ........................... 544/350

[56]  References Cited

U.S. PATENT DOCUMENTS

| 4,443,602 | 4/1984 | Willer | 544/350 |
| 4,503,299 | 3/1985 | Willer | 544/343 |
| 4,614,800 | 9/1986 | Willer | 544/335 |

OTHER PUBLICATIONS

Coon Cliff, "Synthesis of Energetic Materials", Energetic & Technology Review, Jan. Feb. 1988.

Adolph et al, "Synthesis of Energetic Materials" Annual Progress Report for the Office of Naval Research Mar. 1984.

*Primary Examiner*—Charles T. Jordan
*Assistant Examiner*—Anthony R. Chi
*Attorney, Agent, or Firm*—Cushman Darby & Cushman IP Group of Pillsbury Madison & Sutro, LLP

[57]  ABSTRACT

The invention relates to a new process for the synthesis of 2,4,6,8-tetranitro-2,4,6,8-tetraazabicyclo-[3.3.0]octane (bicyclo-HMX) by reaction of nitronium tetrafluoroborate with 2,4,6,8-tetraacetyl-2,4,6,8-tetraazabicyclo[3.3.0]octane in the presence of fluoride ions.

The process makes it possible to obtain pure bicyclo-HMX in an acceptable yield.

Bicyclo-HMX is an explosive which can be employed as explosive or propellent charge in solid pyrotechnic compositions.

10 Claims, No Drawings

PROCESS FOR THE SYNTHESIS OF 2,4,6,8-TETRANITRO-2,4,6,8-TETRAAZABICYCLO (3.3.0) OCTANE

The present invention relates to the field of explosives, especially pulverulent explosives employed as charges in solid pyrotechnic compositions, for example in solid propellants or in explosives containing a plastic binder.

It relates more precisely to a new process for the synthesis of 2,4,6,8-tetranitro-2,4,6,8-tetraazabicyclo[3.3.0] octane, commonly called "bicyclo-HMX" because of its structural analogy with HMX (octogen).

The article "Synthesis Energetic Materials", Energy and Technology Review, Military Application, pages 18 to 22, January–February 1988, mentions, on the one hand, the preparation of a few milligrams of bicyclo-HMX by a 5-stage process and, on the other hand, the potential interest of this compound as explosive when compared with HMX, especially a density estimated to be higher for a safety in use and a stability which are related.

The very low yield obtained and the complexity of the process used make the industrialization of such a process prohibitive.

Numerous investigations have been carried out with the aim of obtaining bicyclo-HMX from 2,4,6,8-tetraacetyl-2,4,6,8-tetraazabicyclo[3.3.0]octane, especially by direct nitrolysis, this potential route being of great interest from an economical and industrial viewpoint.

Despite considerable and durable efforts these investigations have been fruitless.

By way of example, H. G. Adolph and colleagues, in the article "Synthesis of Energetic Materials. Annual Progress Report for the Office of Naval Research", March 1984, DTIC Publication, reference AD-A141495, describe, on pages 11 to 17, the many operating conditions which they have tried unsuccessfully and conclude that the instability and the fragility of the ring, and therefore its opening during the reactions used, is an insurmountable obstacle. Among these fruitless attempts it may be noted that Adolph tried the possible reaction of the abovementioned tetraacetyl derivative with nitronium tetrafluoroborate in acetonitrile medium.

Despite this prejudice, it has unexpectedly been found that, under operating conditions which are very special but also very simple to use, it is possible to obtain bicyclo-HMX directly by nitrolysis of the corresponding tetraactyl derivative, in an acceptable yield and with a highly satisfactory degree of purity by a process which can be industrialized and which is economically advantageous.

The process according to the invention for the synthesis of bicyclo-HMX is characterized in that 2,4,6,8-tetraacetyl-2,4,6,8-tetraazabicyclo[3.3.0]octane is reacted with nitronium tetrafluoroborate in the presence of fluoride ions originating generally from the use, and hence from the presence in the reaction mixture, of an ionic fluoride.

This ionic fluoride is preferably chosen from the group consisting of alkali metal fluorides, alkaline-earth metal fluorides and quaternary ammonium fluorides such as, for example, tetrabutylammonium fluoride or tetraethylammonium fluoride.

In a particularly preferred manner the reaction is carried out in the presence of sodium fluoride or of potassium fluoride.

The starting 2,4,6,8-tetraacetyl-2,4,6,8-tetraazabicyclo [3.3.0]octane is a known compound. For example, in the abovementioned state of the art, Adolph describes its synthesis from diacetyldihydroxyimidazolidine, a known compound which can be obtained by reaction of methylenebisacetamide with glyoxal.

Diacetyldihydroxyimidazolidine is first of all converted into a diacetate derivative (by reaction with acetic acid or anhydride) or into a ditrifluoroacetate derivative (by reaction with trifluoroacetic acid or anhydride).

This diacetate or ditrifluoroacetate derivative is then reacted with methylenebisacetamide, and this makes it possible to obtain the required product.

A better yield is obtained by employing the diacetate derivative in an acetonitrile medium and in the presence of para-toluenesulphonic acid.

According to the invention, as a general rule, the reaction between 2,4,6,8-tetraacetyl-2,4,6,8-tetraazabicyclo[3.3.0] octane and nitronium tetrafluoroborate is carried out in organic solvent medium, preferably in a polar organic solvent medium.

Among the polar organic solvents those particularly preferred are acetonitrile, nitromethane and chlorinated solvents.

According to another preferred alternative form of the invention the reaction temperature is between −30° C. and +50° C., more particularly between 0° and 25° C.

According to another preferred alternative form the molar ratio of nitronium tetrafluoroborate to 2,4,6,8-tetraacetyl-2,4,6,8-tetraazabicyclo[3.3.0]octane is between 5 and 20, preferably between 10 and 15.

According to another preferred alternative form the molar ratio of the ionic fluoride to 2,4,6,8-tetraacetyl-2,4,6,8-tetraazabicyclo[3.3.0]octane is between 2 and 10, preferably between 4 and 8.

According to another preferred alternative form the molar ratio of nitronium tetrafluoroborate to the ionic fluoride is between 1 and 3.

The reaction period may vary, especially as a function of temperature. It may be one of several days.

After hydrolysis of the reaction mixture the bicyclo-HMX formed can be recovered from the liquid phase.

The following nonlimiting example illustrates the invention and the advantages which it offers.

EXAMPLE

A suspension of 13.60 g (102.4 mmol) of nitronium tetrafluoroborate in 55 ml of acetonitrile is cooled to approximately 6° C.

To this suspension are added 2.74 g (47.2 mmol) of potassium fluoride, and then 2.22 g (7.9 mmol) of 2,4,6,8-tetraacetyl-2,4,6,8-tetraazabicyclo[3.3.0]octane obtained by the abovementioned method described by Adolph via diacetyl dihydroximidazolidine diacetate. The mixture is left stirring for 5 d at 10° C.

After cooling to 0° C. the reaction mixture is hydrolysed and then filtered.

The filtrate is recovered after rinsing of the insoluble material with water and then with acetonitrile.

The filtrate is then concentrated with the aid of a rotary evaporator. A solid precipitates. This solid is isolated by filtration. After rinsing with water, this solid is taken up in acetone. The insoluble material is removed by filtration and the acetone filtrate is then evaporated in vacuum. 0.47 g (20% yield) of bicyclo-HMX is obtained in the form of a white solid whose purity, determined by determination by proton NMR, using nitromethane as standard, is close to 96%.

The bicyclo-HMX obtained was identified by mass, $^1$HNMR and $^{13}$C NMR spectrometry in $CD_3COCD_3$, by IR spectrometry and by elemental analysis.

Comparative Example

This comparative example does not form part of the invention. It was carried out solely for the purpose of showing that, according to the invention, the presence of fluoride ions was necessary to obtain the technical effect found.

This comparative test was carried out by reproducing the abovementioned example according to the invention in a strictly identical manner, except that no potassium fluoride was employed.

No trace of bicyclo-HMX could be detected.

This comparative test confirms the abovementioned negative attempts in the state of the art which were made by Adolph and clearly shows the essential part played by the fluoride ions in order that the reaction may take place without opening of the ring.

We claim:

1. Process for the synthesis of 2,4,6,8-tetranitro-2,4,6,8-tetraazabicyclo[3.3.0]octane, characterized in that 2,4,6,8-tetraacetyl-2,4,6,8-tetraazabicyclo[3.3.0]octane is reacted with nitronium tetrafluoroborate in the presence of fluoride ions.

2. Process for synthesis according to claim 1, characterized in that 2,4,6,8-tetraacetyl-2,4,6,8-tetraazabicyclo[3.3.0]octane is reacted with nitronium tetrafluoroborate in the presence of an ionic fluoride.

3. Process for synthesis according to claim 2, characterized in that the ionic fluoride is chosen from the group consisting of alkali metal fluorides, alkaline-earth metal fluorides and quaternary ammonium fluorides.

4. Process for synthesis according to claim 3, characterized in that the ionic fluoride is sodium fluoride or potassium fluoride.

5. Process for synthesis according to claim 1, characterized in that the reaction is carried out in an organic solvent medium.

6. Process for synthesis according to claim 5, characterized in that the organic solvent is a polar organic solvent chosen from the group consisting of acetonitrile, nitromethane and chlorinated solvents.

7. Process for synthesis according to claim 1, characterized in that the reaction temperature is between $-30°$ C. and $+50°$ C.

8. Process for synthesis according to claim 2, characterized in that the molar ratio of nitronium tetrafluoroborate to 2,4,6,8-tetraacetyl-2,4,6,8-tetraazabicyclo[3.3.0]octane is between 5 and 20 and in that the molar ratio of the ionic fluoride to 2,4,6,8-tetraacetyl-2,4,6,8-tetraazahicyclo[3.3.0]octane is between 3 and 9.

9. Process for synthesis according to claim 8, characterized in that the molar ratio of nitronium tetrafluoroborate to the ionic fluoride is between 1 and 3.

10. Process for synthesis according to claim 1, characterized in that after the reaction between nitronium tetrafluoroborate and 2,4,6,8-tetraacetyl -2,4,6,8-tetraazabicyclo[3.3.0]octane the reaction mixture is hydrolysed and then filtered and in that 2,4,6,8-tetranitro-2,4,6,8-tetraazabicyclo[3.3.0]octane is then isolated from the filtrate.

* * * * *